United States Patent [19]

Besançon

[11] Patent Number: 4,485,115
[45] Date of Patent: Nov. 27, 1984

[54] METHOD FOR TREATING DEPRESSIVE SYNDROME BY ADMINISTERING N-(DIETHYLAMINOETHYL)-2-METHOXY-5-METHYLSUFONYL BENZAMIDE

[75] Inventor: Denis Besançon, Paris, France

[73] Assignee: Societe d'Etudes Scientifiques et Industrielles de Lle-de France, Paris, France

[21] Appl. No.: 504,419

[22] Filed: Jun. 15, 1983

[30] Foreign Application Priority Data

Jun. 17, 1982 [FR] France .................................. 8210565

[51] Int. Cl.$^3$ ........................................... A61K 31/165
[52] U.S. Cl. .................................................. 424/324
[58] Field of Search ......................................... 424/324

[56] References Cited

FOREIGN PATENT DOCUMENTS 2305176 4/1979 France .
1364615 8/1974 United Kingdom .
1439295 6/1976 United Kingdom .

OTHER PUBLICATIONS

Chem. Abst., 10th Collective Index, Chem. Substances Azanonaborone–Benzene Ether.

Primary Examiner—Stanley J. Friedman
Attorney, Agent, or Firm—Fitzpatrick, Cella, Harper & Scinto

[57] ABSTRACT

The depressive syndrome associated with alcoholic withdrawal is treated by administering N-(diethylaminoethyl)-2-methoxy-5-methylsulfonyl benzamide.

1 Claim, No Drawings

METHOD FOR TREATING DEPRESSIVE SYNDROME BY ADMINISTERING N-(DIETHYLAMINOETHYL)-2-METHOXY-5-METHYLSUFONYL BENZAMIDE

BACKGROUND OF THE INVENTION

The invention relates to a new use for N-(diethylaminoethyl)-2-methoxy-5-methylsulfonyl benzamide, commonly known as Tiapride. In particular, the invention relates to treating the depressive syndrome associated with alcoholism withdrawal and the like by administering N-(diethylaminoethyl)-2-methoxy-5-methyl-sulfonyl benzamide.

Pharmacological studies have been reported which show that the affinity of Tiapride to dopaminergic receptors is increased, when the receptors are sensitized. Tests conducted in vivo, using as a model, the turning behavior provoked in the mouse by electrolytic lesions of the striatum associated with lesions induced by 6-hydroxydopamine (6-OHDA) have shown that Tiapride antagonizes such behavior. It has been shown that long term administration of ethanol produces hypersensitivity in the dopaminergic receptors. These studies were carried out by producing chronic intoxication by administering young rats with ethanol in increasing concentrations for 270 days and thereafter weaning the rats from the ethanol. Such studies showed an appreciable increase in motor activity in the rats after bilateral application of dopamine in the nucleus accumbens.

There has been a long felt need for an effective treatment for the depressive syndrome arising from withdrawal from alcoholism. Many possible treatments for such a syndrome have been proposed, but to date they have met with generally unsatisfactory results.

SUMMARY OF THE INVENTION

The present invention provides a method for treating the depressive syndrome associated with withdrawal from alcohol comprising administering N-(diethylaminoethyl)-2-methoxy-5-methylsulfonyl benzamide and its pharmacologically acceptable salts in effective amounts.

In another embodiment, it has been found that withdrawal from alcohol increases the activity of an enzyme found in the liver, tryptophan pyrrolase. It has been found that by inhibiting tryptophan pyrrolase activity, one can effectively treat the depressive syndrome associated with withdrawal from alcohol. Accordingly, in another embodiment, the present invention includes a pharmaceutical composition comprising a tryptophan pyrrolase inhibiting amount of N-(diethylaminoethyl)-2-methoxy-5-methylsulfonyl benzamide and its pharmacologically acceptable salts and a pharmaceutically acceptable carrier.

DESCRIPTION OF THE PREFERRED EMBODIMENTS

Certain behavioral disorders have been observed during withdrawal from acute alcoholism. These disorders include irritability and agitation; tremors and gastro-intestinal disorders, insomnia, nausea, loss of appetite and pain due to alcoholic polyneuritis. It has been found that these symptoms can all be linked with hypersensitivity of the dopaminergic receptors. Clinical observations have now confirmed that N-(diethylaminoethyl)-2-methoxy-5-methylsulfonyl benzamide is effective in reducing the symptoms arising from withdrawal from alcohol. Alcoholics suffering from withdrawal symptoms during clinical treatment have been observed to suffer from insomnia, anxiety, and irritability. These symptoms have been alleviated by administration of Tiapride. Alcoholics suffering from the withdrawal syndrome have become nauseous and have lost their appetite. The onset of nausea have been reduced and appetite has been regained upon administration of Tiapride.

The alcoholic often suffers pain from alcoholic polyneuritis. Such pain is soothed by administration of Tiapride.

The overall effect of the administration of Tiapride is to foster in alcoholic patients a greater acceptance of the regimen required to overcome their dependency on alcohol. By reducing the depressive and behavioral disorders arising from withdrawal from alcoholism, treatment for that condition has been dramatically improved.

It is all to well-known that an alcoholic exhibits deep depression during withdrawal. It is now generally understood that such profound changes of mood as observed in man are related to cerebral mechanisms which involve serotonin as a neuromediator. The plasmatic precursor of serotonin is free tryptophan. Accordingly, the availability of serotonin depends in part on the content of its plasmatic precursor. Chronic alcoholism inhibits the activity of the hepatic enzyme, tryptophan pyrrolase, by increasing the NAD(P)H. Withdrawal from alcohol, on the other hand, increases tryptophan pyrrolase activity by a hormone mechanism involving the liberation of corticosterone. The amount of free tryptophan, the serotonin precursor, is thereby reduced. Accordingly, it has been found that during withdrawal from alcohol, there is a marked reduction in the availability of serotonin. This fosters the depressive syndrome.

Accordingly, it is postulated that by reducing the content of tryptophan pyrrolase enzyme, the concentration of free tryptophan can be enhanced. Enhanced concentrations of tryptophan lead to increased concentrations of serotonin. Accordingly, the cerebral mechanisms tending to cause depression are mediated and the syndrome is mitigated.

It has now been found that under certain conditions Tiapride can inhibit the activity of the hepatic enzyme, tryptophan pyrrolase. Clinical studies were conducted which confirmed that Tiapride was effective in treating the depressive syndrome associated with withdrawal from alcohol.

The compound of the invention, Tiapride, and its preparation have been reported in the literature. If desired, Tiapride can be formed into a pharmaceutically acceptable salt by reacting it with a pharmaceutically acceptable inorganic or organic acid, such as hydrochloric, hydrobromic, sulfuric, phosphoric, oxalic, acetic, tartaric, citric or methane-sulfonic. Tiapride can be reacted, if desired, with alkyl sulfates or halides to provide quaternary ammonium salts.

The compound can also be oxidized employing conventional oxidants, such as hydrogen peroxide and manganese dioxide, to give its corresponding N-oxide.

Tiapride can be employed in the form of capsules, tablets, pills, in granulated form or as an injectable solution. The preparation of such medicaments is well-known.

Substances which are inert to Tiapride can be employed to formulate such medicaments, such as lactose, magnesium stearate, starch, talc, cellulose, levilite, alkali metal lauryl-sulfates, saccharin and the other vehicles commonly employed in other medicinal preparations.

The therapeutic benefits of Tiapride may be realized when it is administered in adult doses from about 150-175 milligrams per day, taken in one or more doses. In general an effective dosage is on the order of 2.5 milligrams per kilogram of body weight.

The relatively low toxicity and the absence of undesirable side effects, such as catalepsy, render the compound especially useful in the treatment of the depressive syndrome arising from withdrawal of alcohol from an alcoholic.

The following examples illustrate certain preferred embodiments of the invention and are not indicative of its scope.

EXAMPLE 1

Tests were conducted to illustrate the effects of Tiapride on tryptophan pyrrolase activity in the liver of a rat. Tiapride was administered in doses of 10 milligrams per kilogram, I.P., dissolved in 2 ml of saline solution in male Wistar rats. Tryptophan pyrrolase activity was measured by the micromoles of kynurenine formed per hour per gram of fresh liver. The following Table illustrates holoenzyme activity, total enzyme activity and apoenzyme activity as measured from 0 to 5 hours after administration:

TABLE 1

| Time (hours) | Holoenzyme Activity | Total Enzyme Activity | Apoenzyme Activity |
|---|---|---|---|
| 0 | 2.7 ± 0.26 | 6.3 ± 0.05 | 3.6 ± 0.21 |
| 0.5 | 1.7 ± 0.10 | 3.7 ± 0.27 | 2.0 ± 0.16 |
| 1 | 1.2 ± 0.06 | 2.9 ± 0.22 | 1.7 ± 0.17 |
| 2 | 0.9 ± 0.00 | 2.3 ± 0.06 | 1.4 ± 0.06 |
| 3 | 1.5 ± 0.05 | 3.8 ± 0.47 | 2.3 ± 0.29 |
| 4 | 1.8 ± 0.11 | 4.6 ± 0.14 | 2.8 ± 0.09 |
| 5 | 2.4 ± 0.11 | 6.1 ± 0.64 | 3.7 ± 0.53 |

The test results demonstrate statistically significant reductions in enzyme activity within a half hour after administration of Tiapride and up to about four hours after administration.

EXAMPLE 2

In order to demonstrate the effects of varying the dosage of Tiapride on the activity of tryptophan pyrrolase in the liver of rats, a series of tests were performed in accordance with the procedure of Example 1. Male Wistar rats were injected with varying dosages and tryptophan pyrrolase activity was measured two hours later. The results are presented in Table 2 as follows:

TABLE 2

| Dose (mg/kg) | Holoenzyme Activity | Total Enzyme Activity | Apoenzyme Activity |
|---|---|---|---|
| 0 | 2.7 ± 0.09 | 6.3 ± 0.33 | 3.6 ± 0.25 |
| 0.5 | 1.9 ± 0.07 | 4.3 ± 0.15 | 2.4 ± 0.09 |
| 1 | 1.7 ± 0.02 | 3.0 ± 0.06 | 1.3 ± 0.07 |
| 2.5 | 1.2 ± 0.08 | 2.5 ± 0.11 | 1.3 ± 0.06 |
| 5 | 1.2 ± 0.11 | 2.5 ± 0.11 | 1.3 ± 0.06 |
| 7.5 | 1.2 ± 0.09 | 2.5 ± 0.14 | 1.3 ± 0.07 |
| 10 | 1.1 ± 0.06 | 2.4 ± 0.22 | 1.3 ± 0.19 |

It is clear from the results of this test that Tiapride inhibits tryptophan pyrrolase activity in an effective dose of about 2.5 milligrams per kilogram, corresponding to an adult dose of 150-175 milligrams.

EXAMPLE 3

A clinical study was carried out to determine the degree of effectiveness of Tiapride in inhibiting the depressive syndrome caused by withdrawal from alcohol. The study was carried out in the form of a double blind test comparing the effects of Tiapride and Clometiazole. Clometiazole is a compound commonly used in treatment of alcoholic withdrawal symptoms. The compounds were administered in the following doses:

| | Maximum Quantities Allowed Per Day | | Total Quantities Used On Average Per Day | |
|---|---|---|---|---|
| | Tiapride | Clometiazole | Tiapride | Clometiazole |
| 1st day | 800 mg | 3.072 g | 400 mg | 1.824 g |
| 2nd day | 800 mg | 3.072 g | 700 mg | 2.592 g |
| 3rd day | 600 mg | 2.304 g | 500 mg | 2.112 g |
| 4th day | 450 mg | 1.728 g | 400 mg | 1.536 g |
| 5th day | 300 mg | 1.152 g | 250 mg | 0.96 g |

The patients included in one or the other treatment group were randomly selected. The duration of the study was five days. Each day the depressive state was determined employing the Wakefield Assessment Method. This is a modified and abridged version of the Zung self-assessment scale for depression as published by Zung in 1965. The Wakefield assessment includes 12 items, each marked from 0 to 3, giving a total possible score between 0 and 36. It was found that this method of assessment is reliable when repeated.

Owing to their intoxication, not all patients were able to fill in the assessment scale for the first day. Out of the 16 patients treated with Tiapride on the first day, the average score was 23, while out of the 15 patients treated with Clometiazole on the first day, the average score was 24. On the fifth day of treatment, the average score for the patients treated with Tiapride was 14, while the average score for those treated with Clometiazole was 19. The difference in the final scores obtained is not generally considered statistically significant according to the Mann-Whitney test. However, since the Wakefield assessment is designed to measure endogenous depression and is not fully adapted to daily assessment, the replies to item 1 of the Wakefield assessment were analyzed as an indication of a depressive mood.

In item 1 Wakefield, the statement "I feel wretched and sad" evokes four replies from which the patient may choose; "Yes, absolutely"; "Yes, sometimes"; "Not particularly"; and "Not at all". The following table compares the proportion of patients in the two groups answering a "Yes" to the Wakefield item 1 statement.

TABLE 3

| | Number of Patients | Tiapride % Patients Replying "Yes" | Clometiazole % Patients Replying "Yes" |
|---|---|---|---|
| Day 1 | 31 | 75 | 73 |
| Day 2 | 44 | 59 | 82 |
| Day 3 | 44 | 32 | 55 |
| Day 4 | 45 | 43 | 59 |
| Day 5 | 44 | 30 | 61 |

The average percentage of patients replying "Yes" for the five days in the Tiapride group was 48% whereas for the Clometiazole group the average was 66%. This is a significant difference and illustrates the effectiveness of Tiapride in controlling the depressive syndrome associated with withdrawal from alcohol.

The invention is not to be limited except as set forth in the following claims.

What is claimed is:

1. A method for treating the depressive syndrome associated with withdrawal from alcohol comprising administering to a petient suffering from alcohol withdrawal symptoms N-(diethylaminoethyl)-2-methoxy-5-methylsulfonyl benzamide and the pharmacologically acceptable salts thereof in effective amounts.